(12) United States Patent
Toone et al.

(10) Patent No.: US 6,583,311 B2
(45) Date of Patent: *Jun. 24, 2003

(54) STABLE NO-DELIVERING COMPOUNDS

(75) Inventors: Eric J. Toone, Durham, NC (US); Jonathan S. Stamler, Chapel Hill, NC (US)

(73) Assignee: Duke University, Durham, NC (US)

( * ) Notice: Subject to any disclaimer, the term of this patent is extended or adjusted under 35 U.S.C. 154(b) by 18 days.

This patent is subject to a terminal disclaimer.

(21) Appl. No.: 10/217,580

(22) Filed: Aug. 12, 2002

(65) Prior Publication Data

US 2003/0096862 A1 May 22, 2003

Related U.S. Application Data

(63) Continuation of application No. 10/026,851, filed on Dec. 18, 2001, now Pat. No. 6,488,951, which is a continuation of application No. 09/725,603, filed on Nov. 29, 2000, now Pat. No. 6,359,167, which is a continuation of application No. 09/103,227, filed on Jun. 23, 1998, now Pat. No. 6,207,855.

(51) Int. Cl.$^7$ ...................... C07C 323/03; C07C 207/02; A61N 1/30; A61L 2/20

(52) U.S. Cl. .......................... 560/147; 604/19; 604/187; 604/500; 427/2.1; 422/28

(58) Field of Search .......................... 560/147; 604/500, 604/187, 19; 427/2.1; 422/28; 568/949; 514/645

(56) References Cited

U.S. PATENT DOCUMENTS

| 5,574,068 A | 11/1996 | Stamler et al. ............. 514/562 |
| 5,648,393 A | 7/1997 | Stamler et al. ............. 514/562 |
| 5,650,447 A | 7/1997 | Keefer et al. ............. 514/772.4 |
| 5,770,645 A | 6/1998 | Stamler et al. ............. 524/419 |
| 6,207,855 B1 | 3/2001 | Toone et al. ................ 560/147 |
| 6,359,167 B2 | 3/2002 | Toone et al. ................ 560/147 |

FOREIGN PATENT DOCUMENTS

| WO | WO 92/17445 | 10/1992 |
| WO | WO 95/07691 | 3/1995 |
| WO | WO 98/05689 | 2/1998 |

OTHER PUBLICATIONS

Askew, S.C. et al., Catalysis by $Cu^{2+}$ of nitric oxide release from S–nitrosothiols (RSNO), *J. Chem. Soc. Perkin Trans.* 2:741–745 (1995).

Batsanov, A.S. et al., "Stereocontrol in cyclisation of dioxolanyl radicals," *J. Chem. Soc. Perkin Trans.* 1:1281–1294 (1995).

Goldstein, S. and Czapski, G., "Mechanism of the Nitrosation of Thiols and Amines by Oxygenated •NO Solutions: the Nature of the Nitrosating Intermediates," *J. Am. Chem. Soc.* 118:3419–3425 (1996).

Gorren, A.C.F., et al., "Decomposition of S–Nitrosoglutathione in the Presence of Copper Ions and Gluthathione," *Arch. of Biochem. and Biophys.* 330(2):219–228 (1996).

Roy, B. et al., "New Thionitrites: Synthesis, Stability, and Nitric Oxide Generation," *J. Org. Chem.* 59:7019–7026 (1994).

Vanin, A.F. et al., "Iron Catalyzes both Decomposition and Synthesis of S–Nitrosothiols: Optical and Electron Paramagnetic Resonance Studies," *Nitric Oxide: Biol. and Chem.*, 1(3):191–203 (1997).

Barrett, J. et al., "Photochemistry of the S–Nitroso Derivatives of Hexane–I–thiol and Hexane–I,6–dithiol," *Letters to Nature* 211:848 (1966).

Bauer, J.A. et al., "Chemical Stabilization of a Vasoactive S–Nitrosothiol with Cyclodextrins Without Loss of Pharmacologic Activity," *Pharmaceutical Research* 8(10):1329–1333 (1991).

Dicks, A.P. et al., "The reaction of S–nitrosothiols with thiols at high thiol concentration," *Can. J. Chem.* 76:789–794 (1998).

Le, M. et al., "The Decomposition of S–Nitrosated Dithiols: A Model for Vicinal Nitrosothiols in Enzymes," *Bioorganic & Medicinal Chemistry Letters* 7(11):1393–1398 (1997).

*Primary Examiner*—Carlos Azpuru
(74) *Attorney, Agent, or Firm*—Hamilton, Brook, Smith & Reynolds, P.C.

(57) ABSTRACT

Disclosed are novel NO-releasing compounds which comprise a stabilized S-nitrosyl group and a free alcohol or a free thiol group. Also disclosed is a method of preparing the NO-releasing compounds. The method comprises reacting a polythiol or a thioalcohol with a nitrosylating agent. Also disclosed are medical devices coated with the disclosed compounds, methods of delivering NO to treatments sites in a subject by utilizing the medical devices and methods of sterilizing surfaces.

18 Claims, No Drawings

STABLE NO-DELIVERING COMPOUNDS

RELATED APPLICATIONS

This application is a continuation of application Ser. No. 10/026,851, filed Dec. 18, 2001 now U.S. Pat. No. 6,488,951, which is a continuation of application Ser. No. 09/725,603, now U.S. Pat. No. 6,359,167, filed Nov. 29, 2000 which is a continuation of U.S. application Ser. No. 09/103,227, now U.S. Pat. No. 6,207,855, filed Jun. 23, 1998. The entire teachings of the above applications are incorporated herein by reference.

BACKGROUND OF THE INVENTION

Nitric oxide (referred to herein as "NO") has many uses, including as a medicinal agent. For example, NO has been shown to inhibit smooth muscle proliferation, thrombus formation, platelet aggregation, and smooth muscle contraction. NO can also be used as a bacteriocidal or bacteriostatic agent to sterilize the surfaces of, for example, medical devices. However, the half-life for NO release of most of the known compounds which release NO is less than twelve hours. Thus, most known NO-releasing compounds are too unstable to be useful commercially. The full commercial potential of NO is unlikely to be realized until more stable NO-releasing compounds are developed.

SUMMARY OF THE INVENTION

It has now been found that an S-nitrosyl group (an "—S—NO" group) in a compound generally is stabilized when the compound also has a free thiol group or a free alcohol group. For example, the half-life for NO-release from thiol or alcohol bearing S-nitrosylated compounds is generally greater than about two hundred hours when nitrosylated with between about 0.5 to about 0.7 equivalents of S-nitroso-N-acetyl-D,L-penicillamine (SNAP) (Example 2). In contrast, the half-life for NO release from most S-nitrosylated compounds without free thiols or alcohols is typically less than twelve hours. Based on these results, novel compounds with stabilized S-nitrosylated groups and methods of preparing these compounds are disclosed. Also disclosed are medical devices coated with the disclosed compounds, methods of delivering NO to treatments sites in a subject by utilizing the medical devices and methods of sterilizing surfaces.

One embodiment of the present invention is an NO-releasing compound comprising an S-nitrosyl group and a free alcohol or a free thiol group. The S-nitrosyl group is stabilized with the alcohol or thiol group.

Another embodiment of the present invention is a compound prepared by reacting a polythiol or a thioalcohol with a nitrosylating agent. Preferably, from about 0.5 to about 0.7 equivalents of nitrosylating agent for each free thiol and each free alcohol group in the polythiol or thioalcohol is used. A "polythiol" is a compound with at least two free thiol groups. A "thioalcohol" is a compound with at least one free alcohol and at least one free thiol group.

Yet another embodiment of the present invention is a method of preparing an NO-releasing compound comprising at least one S-nitrosyl group and at least one free alcohol or free thiol group, wherein the S-nitrosyl group is stabilized with the alcohol or thiol group. The method comprises reacting a polythiol or a thioalcohol with a nitrosylating agent. Preferably, from about 0.5 to about 0.7 equivalents of nitrosylating agent for each free thiol and each free alcohol group in the polythiol or thioalcohol are used.

Another embodiment of the present invention is an article which is capable of releasing NO. The article contains (e.g., incorporates or is coated with) at least one of the compounds of the present invention. The article can be a device for which a useful result can be achieved by NO release, including a medical device suitable for implantation at a treatment site in a subject. The medical device can deliver nitric oxide to the treatment site in the subject after implantation. In another example, the article is, for example, a tube or catheter for contacting a bodily fluid of a subject.

Another embodiment of the present invention is a method of delivering nitric oxide to a treatment site in a subject. A medical device which contains one or more of the compounds of the present invention is implanted into the subject at the treatment site.

Another embodiment of the present invention is a method of delivering nitric oxide to a bodily fluid of a subject. The method comprises contacting the bodily fluid with an article, for example a tube or catheter, which contains at least one of the compounds of the present invention.

Yet another embodiment of the present invention is a method of inhibiting the growth of bacteria on surfaces. The method comprises the step of contacting the surface with an effective amount of a compound of the present invention.

The compounds of the present invention have longer half-lives for NO-release than most known NO-releasing compounds. Thus, the compounds of the present invention can be remain at internal treatment sites for longer durations when used as a coating for implantable medical devices and can be stored for longer periods of time than most known NO-releasing compounds. They can also be used as bacteriostatic agents.

DETAILED DESCRIPTION OF THE INVENTION

The NO-releasing compounds of the present invention are small organic molecules. Thus, the compounds of the present invention are comprised primarily of carbon and hydrogen, but can also include other non-metallic elements such as sulfur, oxygen, nitrogen and/or halogens. The compounds of the present invention can contain functional groups which do not substantially increase the rate of NO release, for example, double the rate of release compared with the corresponding compound without the functional group. Examples of suitable functional groups include alcohols, thiols, amides, thioamides, carboxylic acids, aldehydes, ketones, halogens, double bonds, triples bonds and aryl groups (e.g., phenyl, naphthyl, furanyl, thienyl and the like).

As used herein, the term "small organic molecule" excludes macromolecules such as a polypeptides, proteins, or S-nitrosylated polysaccharides or polymers, such as those disclosed in co-pending U.S. Ser. No. 08/691,862. The entire teachings of U.S. Ser. No. 08/691,862 are incorporated herein by reference. The invention also excludes S-nitrosylated derivatives of the compounds represented by Structural Formula (I)–(VII):

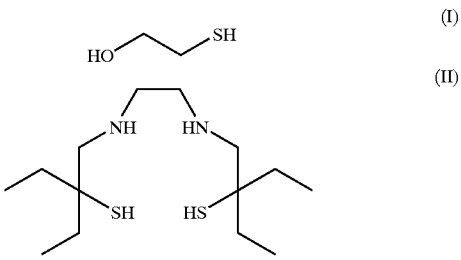

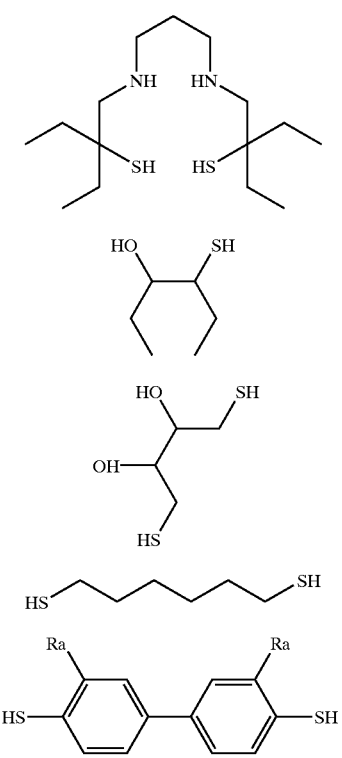

(III)

(IV)

(V)

(VI)

(VII)

Each Ra is —H or methyl and is independently chosen.

As used herein, a "compound with a stabilized S-nitrosyl group" comprises, along with the S-nitrosyl group, a free thiol group or free alcohol group and has a half-life for NO release which is significantly greater than for the corresponding compound with no free thiol or alcohol group (e.g., at least two times greater, and often about ten times greater) when the same nitrosylating agent has been used to prepare both compounds. For example, the half-life for NO release for 6-S-nitrosyl-hexane-1-thiol is about 1800 hours when prepared with SNAP (Example 2), whereas the half-life for NO release for 1-S-nitrosyl-hexane is just over 200 hours when prepared with SNAP. Thus, 6-S-nitrosyl-hexane-1-thiol has a stabilized S-nitrosyl group. Generally, a compound with a stabilized S-nitrosyl group has a half life for NO release greater than about two hundred hours when nitrosylated with between about 0.5 to about 0.7 equivalents of SNAP, and often greater than about one thousand hours.

At least one —S-nitrosyl group in the disclosed compounds is stabilized by the interaction between a free thiol or a free alcohol group and the —S-nitrosyl group. Although Applicants do not wish to be bound by any particular mechanism, this stabilization is consistent with the —S-nitrosyl group and free thiol (or alcohol) existing in equilibrium with a cyclic structure, as shown below in Structural Formula (VIII):

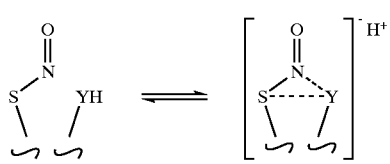

(VIII)

—Y— is —O— or —S—. The "dashed" lines in Structural Formula (VIII) represent a stabilizing interaction, for example, a partial bond between —Y— and the sulfur atom and between —Y— and the nitrogen atom. A stabilizing interaction can be formed, for example, when a free thiol or alcohol is located within three covalent bonds of (alpha to) an S-nitrosyl group. In another example, a stabilizing interaction can be formed when a free thiol or alcohol can be brought within about one to one and a half bond lengths of an S-nitrosyl group by energetically accessible conformational rotations of covalent bonds within the molecule.

Based on the discussion in the previous paragraph, the compounds of the present invention can also be described as comprising one or more of the cyclic structure shown in Structural Formula (VIII). The compounds of the present invention can therefore also be represented by Structural Formula (IX):

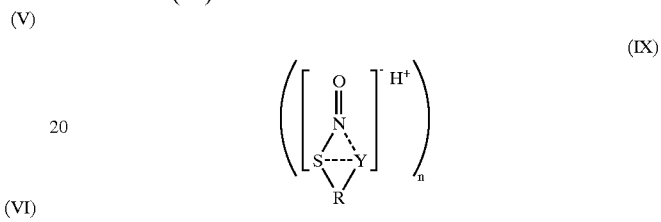

(IX)

—Y— is —S— or —O—.

R is an organic radical. The term "organic radical", as it is used herein, refers to a moiety which comprises primarily hydrogen and carbon, but can also include small amounts of other non-metallic elements such as sulfur, nitrogen, oxygen and halogens. R, when taken together with the one or more stabilized S-nitrosyl groups or the one or more cyclic structures depicted in Strutural Formula (IX), forms a small organic molecule, as described above.

n in Structural Formula (IX) is an integer, preferably from one to about five. When n is greater than 1, the stabilized NO-releasing compound has more than one stabilized —S-nitrosyl group. Each —S-nitrosyl group in a molecule requires a separate free thiol or separate free alcohol for stabilization.

The compounds of the present invention preferably have a molecular weight less than about 1000 atomic mass units (hereinafter "amu"). When the S-nitrosyl group is stabilized by an alcohol group, the compound preferably has a molecular weight greater than about 225 amu and more preferably greater than about 500 amu. When the S-nitrosyl group is stabilized by a thiol group, the compound preferably has a molecular weight greater than about 375 amu, more preferably greater than about 500 amu. When the S-nitrosyl group is stabilized by a thiol group and the compound has a half-life for NO release of greater than about two hundred hours, the compound preferably has a molecular weight greater than about 225 amu.

A polythiol is a small organic molecule which has two or more free thiol groups. Preferably, a polythiol has between about two and about ten free thiol groups.

A thioalcohol is a small organic molecule which has at least one alcohol group and at least one free thiol group. Preferably, a thioalcohol has one to about five free thiol and one to about five free alcohol groups.

As used herein, the terms "polythiol" and "thioalocohol" do not include polypeptides or polythiolated polysaccharides and polymers with pendant thiol groups as described in U.S. Pat. No. 5,770,645. The terms "polythiol" and "thioalcohol" also specifically exclude compounds represented by Structural Formulas (I)–(VII).

Suitable nitrosylating agents are disclosed in Feelisch and Stamler, "Donors of Nitrogen Oxides", *Methods in Nitric*

*Oxide Research* edited by Feelisch and Stamler, (John Wiley & Sons) (1996), the entire teachings of which are hereby incorporated into this application by reference. Suitable nitrosylating agents include acidic nitrite, nitrosyl chloride, compounds comprising an S-nitroso group (S-nitroso-N-acetyl-D,L-penicillamine (SNAP), S-nitrosoglutathione (SNOG), N-acetyl-S-nitrosopenicillaminyl-S-nitroso-penicillamine, S-nitrosocysteine, S-nitrosothioglycerol, S-nitrosodithiothreitol and S-nitrosomercaptoethanol), an organic nitrite (e.g. ethyl nitrite, isobutyl nitrite, and amyl nitrite) peroxynitrites, nitrosonium salts (e.g. nitrosyl hydrogen sulfate), oxadiazoles (e.g. 4-phenyl-3-furoxan-carbonitrile) and the like. The half-life for NO-release of stabilized S-nitrosylated compounds can depend, at least in part, on the nitrosylating agent used in their preparation. For example, the half-life for NO release of stabilized S-nitrosylated compounds prepared with SNAP is generally greater than the corresponding compound prepared with tert-butyl nitrite (Example 2).

To prepare the compounds of the present invention, a polythiol or a thioalcohol is reacted with between about 0.5 to about 0.7 equivalents of nitrosylating agent with respect to each alcohol and thiol. Preferably, nitrosylating agent is added to the polythiol or thioalcohol. For example, to prepare a compound with a stabilized S-nitrosyl group from 1,2-dithioethane or thioethanol, 1.0 mole of nitrosylating agent is added to 1.0 mole of 1,2-dithioethane or thioethanol. S-nitroso-N-acetyl-D,L-penicillamine (SNAP) is a preferred nitrosylating agent. Larger amounts of nitrosylating agent with respect to thiol and/or alcohol groups can be used can be used with certain nitrosylating agents such as S-nitroso-N-acetyl-D,L-penicillamine (SNAP).

The nitrosylation reaction can be carried out neat or in a solvent in which the polythiol or thioalcohol and the nitrosylating agent are soluble. Commonly used solvents include dimethyl sulfoxide (DMSO), dimethyl formamide (DMF) and acetonitrile. Reaction temperatures between about 0° C. and about 50° C., preferably ambient temperature, can be used. Concentrations of polythiol or thioalcohol are generally greater than about 0.01 M. Specific conditions for nitrosylation with SNAP and tert-butylnitrite (TBN) are provided in Example 1.

The reaction with acidic nitrite as the nitrosylating agent can be, for example, carried out in an aqueous solution with a nitrite salt, e.g. $NaNO_2$, $KNO_2$, $LiNO_2$ and the like, in the presence of an acid, e.g. HCl, acetic acid, $H_3PO_4$ and the like, at a temperature from about −20° C. to about 50° C., preferably at ambient temperature.

The reaction with NOCl as the nitrosylating agent can be carried out, for example, in an aprotic polar solvent such as dimethylformamide or dimethylsulfoxide at a temperature from about −20° C. to about 50° C., preferably at ambient temperature.

The formation of stabilized S-nitrosyl groups is disfavored when the polythiol or thioalcohol has substituents, particularly bulky substituents, in close proximity to the stabilizing thiol or alcohol groups. For example, the formation of stabilized S-nitrosyl groups is disfavored when three substituents, for example three alkyl groups, are attached to the carbon atoms alpha or beta to the thiol. Although Applicants do not wish to be bound by any particular mechanism, it is believed that bulky groups in close proximity to a thiol or alcohol can sterically block the interaction between the thiol or alcohol and the the S-nitrosyl group. Thus, —Y— and —S— in stabilized S-nitrosyl groups are preferably bonded to methylene groups.

In a preferred embodiment, the compound is formed by nitrosylating an esterified polyol represented by Structural Formula (X):

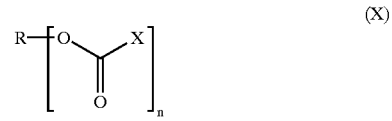

R is an organic radical, as described above.

n in Structural Formula (X) is an integer greater than two, preferably an integer from three to about ten. More preferably, n is an integer from three to about eight.

Each X is independently a thiol-bearing aliphatic group or a substituted thiol-bearing aliphatic group. Preferably, each X is the same thiol-bearing aliphatic group. Examples of suitable thiol-bearing aliphatic groups include —$CH_2SH$, —$CH_2CH_2SH$, —$CH_2CH_2CH_2SH$ and —$CH_2CH_2CH_2CH_2SH$.

The nitrosylation of the esterified polyol is carried out by reacting the esterified polyol with a nitrosylating agent, as described above, preferably with about 0.5 to about 0.7 equivalents of nitrosylating agent per free thiol and free alcohol.

Compounds prepared by nitrosylating an esterified polyol represented by Structural Formula (X) have one or more stabilized S-nitrosyl groups. The compound formed by this reaction is represented by Structural Formula (XI):

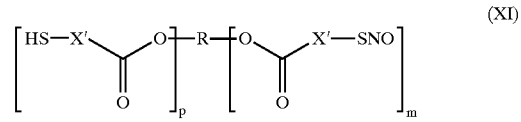

R is an organic radical, as described above.

Each X' is an independently chosen aliphatic group or substituted aliphatic group. Preferably each X' is the same and is a C2–C6 alkyl group, more preferably $CH_2$—, —$CH_2CH_2$—, —$CH_2CH_2CH_2$— or —$CH_2CH_2CH_2CH_2$—.

p and m are positive integers such that p+m is greater than two. Preferably, p+m is less than or equal to about 10. Even more preferably, p+m are less than or equal to six.

Specific examples of polythiols and thioalcohols which have been nitrosylated to form compounds with stable S-nitrosyl groups are shown in the Table in Example 2. Also shown in the Table are the half-life for NO-release for each S-nitrosylated compound and the nitrosylating agent used to prepare each compound.

Compounds represented by Structural Formula (XI) can form polymers, which can be used to coat medical devices for delivering NO in vivo. These polymers are disclosed in co-pending U.S. Pat. No. 6,232,434, filed on Jun. 23, 1998, the entire teachings of which are incorporated herein by reference.

As used herein, aliphatic groups include straight chained, branched or cyclic $C_1$–$C_8$ hydrocarbons which are completely saturated or which contain one or more units of unsaturation. Suitable substituents for an aliphatic group are those which: 1) are substantially inert with respect to —S-nitrosyl groups, i.e., groups which do not substantially increase the rate, e.g., double the rate of NO release from NO-releasing molecules; and 2) do not substantially interfere with the nitrosylation of free thiol groups, i.e. do not substantially decrease the yield of the nitrosylation or cause the formation of significant amounts of by-products.

Examples of suitable substituents include halogens, C1–C5 straight or branched chain alkyl groups, alcohols, carboxylic acids, amides, thioamides, and the like.

Another embodiment of the present invention is a method of delivering NO to a treatment site in a subject using the novel compositions of the present inventions to deliver NO. A "treatment site" includes a site in the body of a subject in which a desirable therapeutic effect can be achieved by contacting the site with NO. A "subject" refers to a human or an animal such as a veterinary animal (e.g., dogs, cats and the like) and farm animals (e.g., horses, cows, pigs and the like).

Treatment sites are found, for example, at sites within the body which develop restenosis, injury or thrombosis as a result of trauma caused by contacting the site with a synthetic material or a medical device. For example, restenosis can develop in blood vessels which have undergone coronary procedures or peripheral procedures with PTCA balloon catheters (e.g. percutaneous transluminal angioplasty). Restenosis is the development of scar tissue from about three to six months after the procedure and results in narrowing of the blood vessel. NO reduces restenosis by inhibiting platelet deposition and smooth muscle proliferation. NO also inhibits thrombosis by inhibiting platelets and can limit injury by serving as an anti-inflammatory agent.

A site in need of treatment with NO often develops at vascular sites which are in contact with a synthetic material or a medical device. For example, stents are often inserted into blood vessels to prevent restenosis and re-narrowing of a blood vessel after a procedure such as angioplasty. Platelet aggregation resulting in thrombus formation is a complication which may result from the insertion of stents. NO is an antiplatelet agent and can consequently be used to lessen the risk of thrombus formation associated with the use of these medical devices. Other examples of medical devices which contact vascular sites and thereby increase the risk of thrombus formation include sheaths for veins and arteries and GORE-TEX surgical prostheses.

The need for treatment with NO can also develop at non-vascular sites, for example at sites where a useful therapeutic effect can be achieved by reducing an inflammatory response. Examples include the airway, the gastrointestinal tract, bladder, uterine and corpus cavernosum. Thus, the compositions, methods and devices of the present invention can be used to treat respiratory disorders, gastrointestinal disorders, urological dysfunction, impotence, uterine dysfunction and premature labor. NO delivery at a treatment site can also result in smooth muscle relaxation to facilitate insertion of a medical device, for example in procedures such as bronchoscopy, endoscopy, laparoscopy and cystoscopy. Delivery of NO can also be used to prevent cerebral vasospasms post hemorrhage and to treat bladder irritability, urethral strictures and biliary spasms.

The need for treatment with NO can also arise external to the body in medical devices used to treat bodily fluids temporarily removed from body for treatment, for example blood. Examples include conduit tubes within heart lung machines, tubes of a dialysis apparatus and catheters.

The method of delivering NO to a treatment site in a subject contains implanting a medical device which comprises one or more compounds of the present invention at the treatment site. NO can be delivered to bodily fluids, for example blood, by contacting the bodily fluid with a tube or catheter comprising one or more compounds of the present invention. Examples of treatment sites in a subject, medical devices suitable for implementation at the treatment sites and medical devices suitable for contacting bodily fluids such as blood are described in the paragraphs hereinabove.

"Implanting a medical device at a treatment site" refers to bringing the medical device into actual physical contact with the treatment site or, in the alternative, bringing the medical device into close enough proximity to the treatment site so that NO released from the medical device comes into physical contact with the treatment site. A bodily fluid is contacted with a medical device, e.g., a tube or cather, which comprises one or more compounds of the present invention when, for example, the bodily fluid is temporarily removed from the body for treatment by the medical device, and the coating is an interface between the bodily fluid and the medical device. Examples include the removal of blood for dialysis or by heart lung machines.

An article, for example a medical device such as a stent, tube or catheter, can be coated with one or more compounds of the present invention. A mixture is formed by combining a solution comprising a dithiol or thioalcohol with an article insoluble in the solution. The mixture is then combined with a nitrosylating agent under conditions suitable for nitrosylating free thiol groups, resulting in formation of a stabilized NO-releasing compound. When the stabilized NO-releasing compound is insoluble in solution, the NO-releasing compound precipitates from the solution and coats the article. When the stabilized NO-releasing compound is soluble in the solution or when the nitrosylation reaction is carried out in a polar aprotic solvent such as dimethylformamide (DMF) or dimethylsulfoxide (DMSO), the article can be dipped into or sprayed with the reaction mixture and then dried in vacuo or under a stream of an inert gas such as nitrogen or argon, thereby coating the article. Suitable nitrosylating agents include SNAP, tert-butyl nitrite, acidified nitrite, S-nitrosothiols, organic nitrite, nitrosyl chloride, oxadiazoles, nitroprusside and other metal nitrosyl complexes, peroxynitrites, nitrosonium salts (e.g. nitrosyl hydrogensulfate) and the like.

It is to be understood that other methods of applying coatings to devices, including methods known in the art, can be used to coat articles with the compounds of the present invention.

An article incorporates an NO-releasing compound of the present invention when the compound is "entrapped" within the molecular framework of a material which is part of the article. For example, many medical devices include certain polymers. An NO-releasing compound can be incorporated into these polymers by carrying out the polymerization reaction through which these polymers are formed in the presence of an NO-releasing compound. The NO-releasing compound is thereby entrapped in the molecular framework of the resulting polymer product, which can then be used to prepare the medical device.

An article also incorporates an NO-releasing compound when the NO-releasing compound is chemically bonded to a material which is part of the article.

It is to be understood that other methods of incorporating compounds into compositions are known in the art and can be used to incorporate the compounds of the present invention into the materials used to produce medical devices.

The NO-releasing compounds of the present invention are bacteriostatic (Example 3). Thus, these compounds can be used to inhibit the growth of bacteria on surfaces, for example, the surfaces of medical devices or medical furniture prior to use. "Inhibiting the growth of bacteria" refers to a statistically significant lower bacteria count on a surface after application of the compound compared with a similar surface which has not been treated with the compound. The NO-releasing compound is applied to a surface in need of sterilization by, for example, dissolving the compound in a non-toxic solvent at concentrations between about 0.01 M and 5.0 M. The solution is then applied to the surface by spraying, wiping or pouring the resulting solution onto said surface. A quantity of solution sufficient to cover the surface is generally used. The solution is allowed to remain in contact with the surface for as long as inhibition of bacteria growth is required. The solution and any residues are removed, for example, by wiping or washing with a solvent suitable for dissolving the NO-releasing compound and any decomposition products.

The invention is further illustrated by the following examples, which are not intended to be limiting in any way.

EXEMPLIFICATION

All precursor thiols were obtained from Sigma-Aldrich Chemical Co. and were used without further purification. Tertiary-butyl nitrite (TBN, 96%) and N-acetyl-D,L-penicillamine were purchased from Aldrich Chemical Co. and were used without further purification. Dimethylsulfoxide (DMSO) was purchased from Mallinckrodt, passed through a CHELEX 100 column and bubbled for thirty minutes with argon prior to use. Dimethylformamide (DMF) was purchased from VWR Scientific.

S-Nitrosyl-N-acetyl-D,L-penicillamine (SNAP) was prepared by mixing a 0.2 M solution of N-acetyl-D,L-penicillamine in 1:1 methanol/1 N HCl with an equimolar amount of sodium nitrite in water. SNAP precipitated out of solution as a green solid, which was filtered and washed with water prior to use.

EXAMPLE 1

Preparation of Stabilized S-Nitrosylated Compounds

S-nitrosylated compounds were prepared by adding TBN to a polythiol or thioalcohol. Alternatively, S-nitrosylated compounds were prepared by adding a polythiol or thioalcohol to a solution of SNAP in DMF (0.12 M is a representative concentration). All reactions were carried out at room temperature. 0.5 equivalents of nitrosylating agent per thiol group (or per alcohol and thiol group) were used. All reactions were carried out under argon in the dark. A rapid color change to red was observed after addition of the nitrosylating agent. Stirring was continued for approximately another two to five minutes after the color change.

S-nitrosylated compounds were characterized by $^{15}N$ NMR and by their UV/visible absorbance spectra. The $^{15}N$ NMR spectrum of stabilized S-nitrosylated compounds showed a singlet at about 424 ppm relative to $HNO_3$. In contrast, the $^{15}N$ NMR spectrum of S-nitrosylated tertiary butyl thiol prepared according to the procedure described above gave a singlet at 480 ppm relative to $HNO_3$. The UV/visible absorbance spectrum of stabilized S-nitrosylated compounds gave an absorbance maximum between about 540 and 555 nanometers.

EXAMPLE 2

Half-Lives for NO Release From Stabilized S-Nitrosylated Compounds

The half-lives for NO release from the stabilized S-nitrosylated compounds of the present invention were determined by monitoring the decrease in intensity of the absorbance maximum between 540 and 555 nanometers over time. When the nitrosylation reaction was performed neat, the uv/visible absorbance spectrum was obtained by adding several drops of the reaction mixture to a cuvette containing DMSO. When the nitrosylation was carried out in solution, the absorbance spectrum was obtained directly from the reaction mixture. Data for these plots were obtained by performing at least three absorbance scans to create a linear plot from which half-lives were determined. Kinetics runs were performed in the dark under an argon atmosphere. A Hewlett-Packard 8452A Diode Array Spectrophotometer in conjunction with HP89531A MS-DOS UV/VIS Operating Software was utilized to obtain kinetic data for use in half-life determinations.

The Table shows the half-lives for NO release of a number of stablized S-nitrosylated polythiols and thioalcohols prepared according to the procedures described in Example 1. The Table indicates whether the half-life determination was for an S-nitrosylated compound prepared with SNAP or TBN. Only approximate values could be determined when the half-life was greater than one thousand hours.

The Table also shows that the half-live for NO release for S-nitrosylated hexane thiol prepared with SNAP according to the procedure described above is 280 hours and that the half-life for NO release of 1-S-nitrosyl hexane 6-thiol prepared with SNAP is about 1800 hours. This result demonstrates the stabilizing effect of the free thiol group.

As can be seen from the Table, longer half-lives are generally obtained when SNAP was used as the nitrosylating agent. S-Nitrosylated compounds obtained from SNAP in the Table generally have half-lives greater than two hundred hours.

TABLE

| Compound | Half-Life For NO-Release in Hours: | |
|---|---|---|
| | TBN[1] | SNAP[2] |
| HS–CH₂CH₂–SHH | 104 | 225 |
| [HS–CH₂CH₂–C(O)–O–]₄ | 87 | 570 |
| HS–C(O)–O–...–O–C(O)–SH (branched with SH) | 84 | 618 |
| HS–C(O)–O–CH₂CH₂–O–C(O)–SH | 108 | |
| [–O–C(O)–CH₂CH₂–SH]₃ | 126 | 440 |
| HS–CH₂–CH(OH)–C(O)H | 167 | 170 |

TABLE-continued

| Compound | Half-Life For NO-Release in Hours: | |
|---|---|---|
| | TBN[1] | SNAP[2] |
| HS–(CH2)–SHH (structure) | 196 | 1500[3] |
| HS–CH2CH2–O–C(=O)–CH3 (structure) | 105 | 228 |
| [HS–CH2–C(=O)–O–]3 branched ester (structure) | 82 | 618 |
| HO–C(=O)–CH(SH)–CH2–C(=O)–OH (structure) | 386 | 2200[3] |
| HS–(CH2)–SHH (structure) | 33 | 150 |
| HS–CH2CH2–O–CH2CH2–SHH (structure) | 48.8 | 1300[3] |
| HS–(CH2)4–SHH (structure) | 207.2 | 1800[3] |
| dimethylbenzene-di-CH2SH (structure) | | 188 |
| alkyl–SHH (structure) | | 280 |

[1]Half-life for NO release when the compound is nitrosylated with TBN
[2]Half-life for NO release when the compound is nitrosylated with SNAP
[3]Approximate half-lives

EXAMPLE 3

Nitrosylated 3-Mercapto-1,2-Propanediol is Bacteriostatic

Nitrosated 3-mercapto-1,2-propanediol was prepared with TBN bed in the Example 1. The nitrosylated compound was dissolved in 10 mL of deionized water (0.16 M) that had been passed through a CHELEX 100 column and bubbled with argon for 30 minutes. The resulting solution was red.

E. coli cells (pTC 190) were plated onto the culture plates and grown overnight at 40° C. The E. coli cells contained a plasmid encoding for ampicillin resistance. The solution was then sprayed onto a culture plate (LB/Amp/Glucose). After 24 hours, this plate showed the growth of a few colonies, all localized on one side of the plate.

A growth plate coated only with E. coli cells displayed a continuous lawn of growth after 24 hours. This plate was then sprayed with the nitrosylated compound solution at the 24$^{th}$ hour. After another 24 hours the plate contained a lawn of colonies that was approximately as dense as prior to application of the S-nitrosylated compound.

A control plate that was not coated with the nitrosylated compound solution nor plated with E. coli cells showed no bacterial growth. A second control plate that was not plated with E. coli cells but coated with the nitrosylated compound solution showed no bacterial colony growth.

These results show that nitrosylated 3-mercapto-1,2-propanediol is bacteriostatic.

EXAMPLE 4

Reaction of 1,6-Hexanedithiol and 1-Hexanethiol With SNAP 1,6-Hexanedithiol (25 uL, 24.6 mg, 0.164 mmol) was dissolved in 6.0 mL of DMSO in 11 separate 10-mL test tubes. S-Nitroso-N-acetylpenicillamine (SNAP) was added in incremental stoichiometric amounts to each test tube as follows:

| mg SNAP | equivalents SNAP |
|---|---|
| 9.0 | 0.25 |
| 18.0 | 0.5 |
| 27.0 | 0.75 |
| 36.0 | 1.0 |
| 45.0 | 1.25 |
| 54.0 | 1.5 |
| 63.0 | 1.75 |
| 72.0 | 2.0 |
| 108.0 | 3.0 |
| 144.0 | 4.0 |
| 180.0 | 5.0 |

The samples were stored under ambient atmosphere in the dark. Absorbance values were taken at time intervals in a 1-cm path length quartz cell at wavelengths of 520, 554, and 594 nm. While the absorbance readings were being taken, the samples were under ambient light for approximately 1 hour.

1-Hexanethiol (25 uL, 21.0 mg, 0.177 mmol) was dissolved in 6.0 mL of DMSO in 9 separate 10-mL test tubes. S-Nitroso-N-acetylpenicillamine (SNAP) was added in incremental stoichiometric amounts to each test tube as follows:

| mg SNAP | equivalents SNAP |
|---|---|
| 9.8 | 0.25 |
| 19.5 | 0.5 |
| 29.3 | 0.75 |
| 39.0 | 1.0 |
| 48.8 | 1.25 |
| 58.5 | 1.5 |
| 78.0 | 2.0 |
| 117.0 | 3.0 |
| 156.1 | 4.0 |

The samples were stored under ambient atmosphere in the dark. Absorbance values were taken at time intervals in a 1-cm path length quartz cell at wavelengths of 520, 554, and 594 nm. While the absorbance readings were being taken, the samples were under ambient light for approximately 1 h.

In both reactions, a red color corresponding to an absorbance at 554 nm appeared almost immediately after the reagents are mixed. The red color peaked at the same maximum value about three hours after mixing for both 1-hexanethiol and 1,6-hexanedithiol when 0.5 equivalents or more of SNAP are used. This result is consistent with the formation of a stabilized S-nitrosylated compound, i.e., the nitrosylation of only one of the thiol groups in 1,6-hexanedithiol, even when more than 0.5 equivalents of SNAP are present.

When the experiment was repeated with TBN or acidic nitrite in place of SNAP, the absorbance peak at 554 nm for the reaction with 1,6-hexanedithiol increased as the amount of nitrosylating used increased, up to 1.0 equivalent of nitrosylating agent per thiol group. This result is consistent with the formation of stabilized S-nitrosylated when 0.5 equivalents of TBN or acidic nitrite were used, and with nitrosylation of the second thiols group when more than 0.5 equivalents of TBN or acidic nitrite were used.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed:

1. A compound containing at least one stabilized S-nitrosyl group and at least one free thiol group or free alcohol group, wherein the S-nitrosyl group is stabilized by the free alcohol group or the free thiol group and wherein the compound has a half-life for NO-release that is at least two times as great as the corresponding compound without the free thiol group or free alcohol group, wherein the compound is prepared by reacting a polythiol or a thioalcohol with a nitrosylating agent, with the proviso that the polythiol or thioalcohol is not a polypeptide, an unsubstituted straight chained or branched dithiolated alkane, an unsubstituted straight chained or branched thioalkanol, a polythiolated polysaccharide, or a polymer with pendant thiol groups and is not represented by one of the following structural formulas:

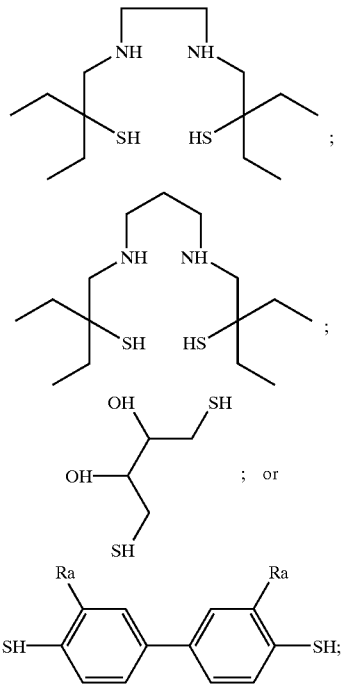

wherein each Ra is —H or methyl and is independently chosen.

2. The compound of claim 1 wherein 0.5 to 0.7 equivalents of nitrosylating agent per free thiol and per free alochol in the polythiol or thialcohol is used.

3. The compound of claim 2 wherein the nitrosylating agent is reacted with a thioalcohol and the compound has a molecular weight of at least 225 atomic mass units.

4. The compound of claim 3 wherein the compound has a molecular weight less than 1000 atomic mass units.

5. The compound of claim 4 wherein the alcohol and thiol are both primary.

6. The compound of claim 2 wherein the nitrosylating agent is reacted with a polythiol and the compound has a molecular weight greater than 375 atomic mass units.

7. The compound of claim 6 wherein the compound has a molecular less than 1000 atomic mass units.

8. The compound of claim 7 wherein both thiols are primary.

9. The compound of claim 1 wherein the nitrosylating agent is S-nitroso-N-acetyl-D,L-penicillamine.

10. A method of preparing a compound containing a stabilized S-nitrosyl group and a free thiol group or free alcohol group, wherein the S-nitrosyl group is stabilized by the free alcohol group or the free thiol group and wherein the compound has a half-life for NO-release that is at least two times as great as the corresponding compound without the free thiol group or free alcohol group, said method comprising the step of reacting a polythiol or a thioalcohol with a nitrosylating agent, with the proviso that the polythiol or thioalcohol is not a polypeptide, an unsubstituted straight chained or branched dithiolated alkane, an unsubstituted straight chained or branched thioalkanol, a polythiolated polysaccharide, or a polymer with pendant thiol groups and is not represented by one of the following structural formulas:

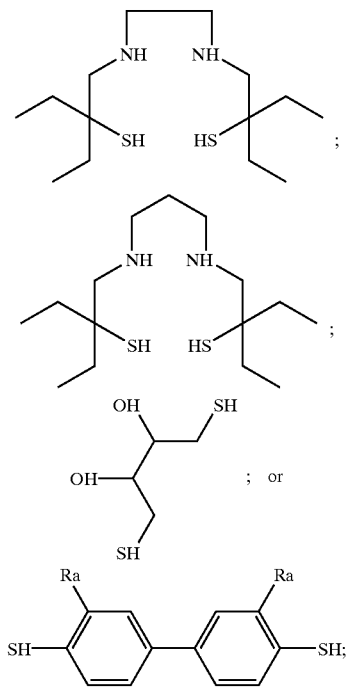

wherein each Ra is —H or methyl and is independently chosen.

11. The method of claim 10 wherein 0.5 to 0.7 equivalents of nitrosylating agent per free thiol and per free alcohol in the polythiol or thialcohol is used.

12. The method of claim 11 wherein the nitrosylating agent is reacted with a thioalcohol and the compound has a molecular weight of at least 225 atomic mass units.

13. The method of claim 12 wherein the compound has a molecular weight less than 1000 atomic mass units.

14. The method of claim 13 wherein the alcohol and thiol are both primary.

15. The method of claim 11 wherein the nitrosylating agent is reacted with a polythiol and the compound has a molecular weight greater than 375 atomic mass units.

16. The method of claim 15 wherein the compound has a molecular less than 1000 atomic mass units.

17. The method of claim 16 wherein both thiols are primary.

18. The method of claim 10 wherein the nitrosylating agent is S-nitroso-N-acetyl-D,L-penicillamine.

* * * * *